(12) United States Patent
Gostein et al.

(10) Patent No.: US 10,312,859 B2
(45) Date of Patent: Jun. 4, 2019

(54) OPTICAL SOILING MEASUREMENT DEVICE FOR PHOTOVOLTAIC ARRAYS

(71) Applicants: Michael Gostein, Austin, TX (US); William Stueve, Austin, TX (US)

(72) Inventors: Michael Gostein, Austin, TX (US); William Stueve, Austin, TX (US)

( * ) Notice: Subject to any disclaimer, the term of this patent is extended or adjusted under 35 U.S.C. 154(b) by 0 days.

(21) Appl. No.: 15/877,207

(22) Filed: Jan. 22, 2018

(65) Prior Publication Data

US 2018/0331653 A1 Nov. 15, 2018

Related U.S. Application Data

(60) Provisional application No. 62/505,343, filed on May 12, 2017, provisional application No. 62/510,347, filed on May 24, 2017.

(51) Int. Cl.

| | |
|---|---|
| *G01N 21/00* | (2006.01) |
| *H02S 50/15* | (2014.01) |
| *H02S 50/00* | (2014.01) |
| *G01N 21/47* | (2006.01) |
| *H02S 40/10* | (2014.01) |
| *G01N 21/94* | (2006.01) |
| *G01N 15/06* | (2006.01) |
| *H02S 40/30* | (2014.01) |
| *G01N 21/552* | (2014.01) |
| *G01N 21/15* | (2006.01) |
| *G01N 15/00* | (2006.01) |

(52) U.S. Cl.
CPC ......... *H02S 50/15* (2014.12); *G01N 15/0612* (2013.01); *G01N 21/47* (2013.01); *G01N 21/94* (2013.01); *H02S 40/10* (2014.12); *H02S 50/00* (2013.01); *G01N 21/552* (2013.01); *G01N 2015/0046* (2013.01); *G01N 2021/157* (2013.01); *G01N 2021/4735* (2013.01); *G01N 2201/061* (2013.01); *H02S 40/30* (2014.12)

(58) Field of Classification Search
CPC .. G01N 21/958; G01N 21/3554; G01N 21/94; G01N 21/896; G01N 2021/435; G01N 2021/945; G01N 27/048; B60S 1/0833
USPC ............ 356/239.1, 445, 239.2, 239.8, 237.2; 250/339.1
See application file for complete search history.

(56) References Cited

U.S. PATENT DOCUMENTS

| | | |
|---|---|---|
| 3,947,131 A | 3/1976 | Karl |
| 4,605,302 A | 8/1986 | Lofgren |
| 4,737,629 A | 4/1988 | Iwama |
| 4,803,470 A | 2/1989 | Fineman |
| 4,808,813 A | 2/1989 | Champetier |

(Continued)

FOREIGN PATENT DOCUMENTS

| | | |
|---|---|---|
| WO | WO 87/07023 | 11/1987 |
| WO | WO 95/24635 | 9/1995 |

*Primary Examiner* — Hoa Q Pham

(57) ABSTRACT

A device comprising a transparent window, a photoemitter, a photodetector, and a measurement unit, wherein said photoemitter is configured to illuminate soiling particles accumulating on a surface of said transparent window, said photodetector is configured to generate a signal based on detection of light that passes through said transparent window and reflects and/or scatters from said soiling particles, and said measurement unit determines a soiling level of said transparent window based upon a measurement of said signal.

11 Claims, 8 Drawing Sheets

(56) References Cited

U.S. PATENT DOCUMENTS

| | | | | |
|---|---|---|---|---|
| 4,871,917 A | * | 10/1989 | O'Farrell | B60S 1/0822 |
| | | | | 250/341.7 |
| 4,960,996 A | * | 10/1990 | Hochstein | B60S 1/0822 |
| | | | | 15/250.001 |
| 5,812,270 A | | 9/1998 | Hampton | |
| 6,404,490 B2 | * | 6/2002 | Blasing | B60S 1/0822 |
| | | | | 250/227.25 |
| 7,253,898 B2 | * | 8/2007 | Saikalis | B60S 1/0822 |
| | | | | 250/201.1 |
| 7,348,586 B2 | | 3/2008 | Ishikawa | |
| 2002/0190195 A1 | | 12/2002 | O'Connor | |
| 2005/0030529 A1 | * | 2/2005 | Schuler | B60S 1/0822 |
| | | | | 356/239.8 |
| 2011/0007047 A1 | | 1/2011 | Fujioka | |
| 2011/0085161 A1 | | 4/2011 | Thien | |
| 2011/0122423 A1 | * | 5/2011 | Jones | G01B 11/0683 |
| | | | | 356/630 |
| 2014/0104072 A1 | | 4/2014 | Temming | |
| 2015/0355017 A1 | | 10/2015 | SunEdison | |
| 2018/0331654 A1 | * | 11/2018 | Gostein et al. | H02S 50/15 |

\* cited by examiner

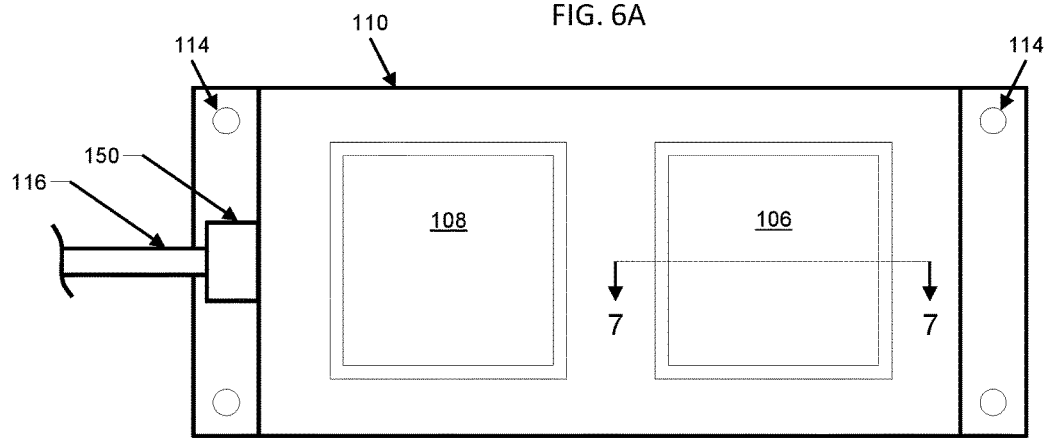
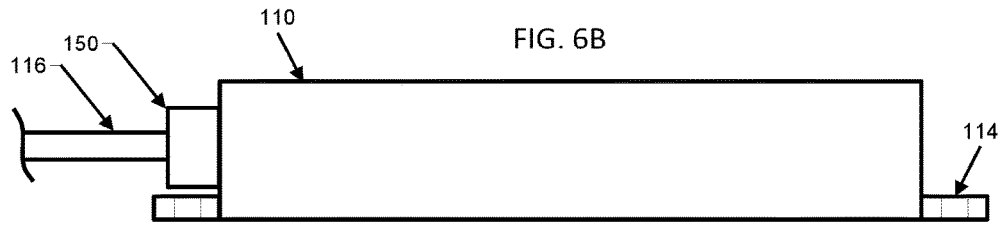

OPTICAL SOILING MEASUREMENT DEVICE FOR PHOTOVOLTAIC ARRAYS

CROSS-REFERENCE TO RELATED APPLICATIONS

This application claims the benefit of U.S. Provisional Patent Application No. 62/505,343, filed on May 12, 2017, entitled "Optical Soiling Measurement Device for Photovoltaic Arrays" and naming Gostein and Stueve as inventors. The above-referenced patent application is hereby incorporated by reference herein in its entirety.

This application claims the benefit of U.S. Provisional Patent Application No. 62/510,347, filed on May 24, 2017, entitled "Soiling Measurement Device for Photovoltaic Arrays Employing Microscopic Imaging" and naming Gostein and Stueve as inventors. The above-referenced provisional patent application is hereby incorporated by reference herein in its entirety.

The subject matter of the present application is related to the subject matter of the commonly assigned, co-pending U.S. patent application Ser. No. 15/877,351, filed on Jan. 22, 2018, the same day as the present application, entitled "Soiling Measurement Device for Photovoltaic Arrays Employing Microscopic Imaging" and naming Gostein and Stueve as inventors. The above-referenced patent application is hereby incorporated by reference herein in its entirety.

FIELD OF THE INVENTION

The disclosed subject matter is directed to the measurement of soiling levels of photovoltaic (PV) arrays.

SUMMARY

In one respect, disclosed is a device comprising a transparent window, a photoemitter, a photodetector, and a measurement unit, wherein said photoemitter is configured to illuminate soiling particles accumulating on a surface of said transparent window, said photodetector is configured to generate a signal based on detection of light that passes through said transparent window and reflects and/or scatters from said soiling particles, and said measurement unit determines a soiling level of said transparent window based upon a measurement of said signal.

BRIEF DESCRIPTION OF THE DRAWINGS

FIG. 6A depicts a top view of an embodiment comprising a soiling sensor and irradiance sensor within an enclosure.

FIG. 6B depicts side views of an embodiment depicted in FIG. 6A.

DETAILED DESCRIPTION OF THE INVENTION

Figure 1:
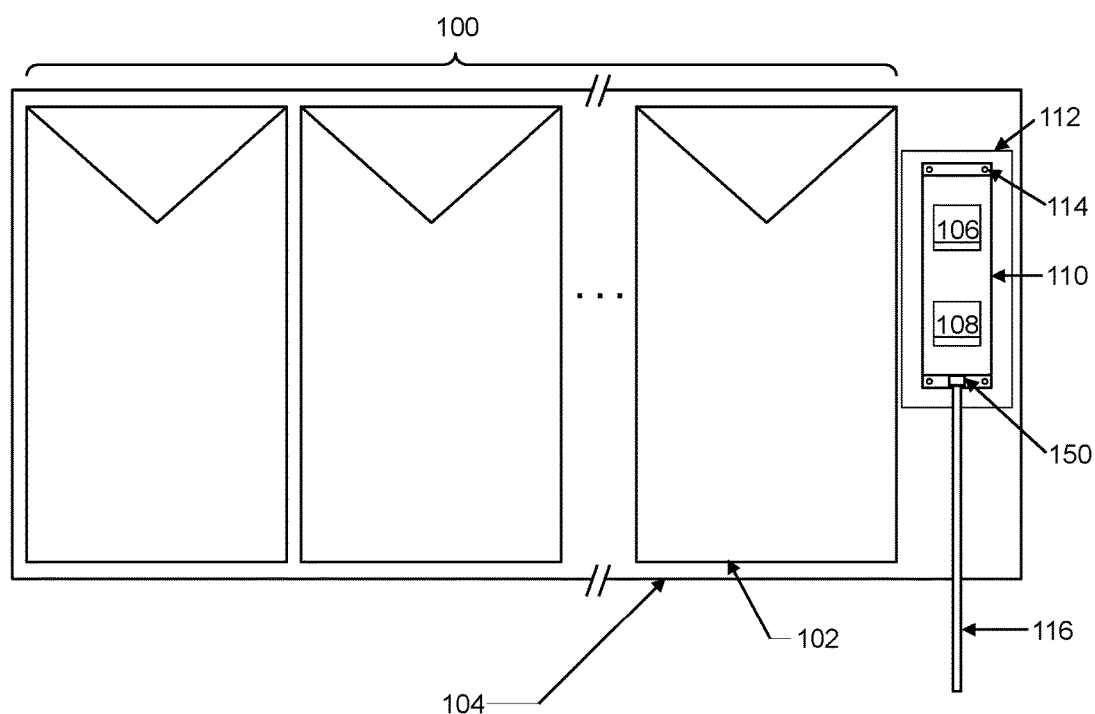
FIG. 1 depicts an embodiment comprising a soiling sensor and irradiance sensor within an enclosure mounted within a PV array.

Solar panels, also known as photovoltaic (PV) modules, are used to convert sunlight to electric power in installations known as PV arrays. An important loss factor for a PV array is the accumulated deposition of airborne particulate matter on the light-receiving surfaces of the PV modules. This accumulation, known as soiling, reduces the power output of a PV array by blocking the transmission of sunlight to the PV cells of the PV array. Soiling particles consist of any airborne particulate matter, such as dust, dirt, soot, pollen, etc., which deposits on a PV array, and have typical diameters ranging from ~0.2 microns to ~200 microns. In dusty outdoor regions without frequent rainfall, the power loss due to soiling, known as soiling loss, can be significant.

In commercial electric power generation applications, which range from small ground-mounted and roof-mounted PV arrays to large utility-scale projects, owners and operators of PV arrays often wish to measure losses due to soiling. Motivations include, but are not limited to, pre-construction assessment of soiling loss as an aid to site selection and performance estimation, validation and monitoring of the performance of an operating PV array, and determination of when to wash a PV array in order to yield greatest return on investment for the expense of washing.

The soiling level, also called soiling loss or transmission loss, is the loss due to soiling particles in the usable light received by the PV cells of the PV array, relative to a clean state. In some embodiments, the soiling level may be defined as the fractional loss in the usable light received, relative to a clean state. Usable light means light that is absorbed by the PV array and is converted, or could be converted, to electrical output. Equivalently, the soiling level can be defined as one minus the fractional transmission of usable light through the layer of soiling particles, relative to a clean state. In the absence of soiling particles the transmission so defined, in some embodiments, is 100% and soiling level is 0%, i.e. transmission is defined relative to the clean state of the device ignoring any other losses not due to soiling. The soiling ratio is defined as the ratio of the PV array electrical output to its expected output in a clean state, or, equivalently, as the fractional transmission of usable light. The measurement of any of soiling level, soiling loss, transmission loss, transmission, or soiling ratio is equivalent, as each is an expression of the loss due to soiling. It should be noted that soiling level, soiling loss, transmission loss, transmission, or soiling ratio may also be defined using alternative mathematical functions and/or scales, where such scales include for example fractional values, percentages, logarithmic scales, units of power, and units of energy, and that each of these alternative terms, mathematical functions, and/or scales is intended to be within the scope of this disclosure.

In some embodiments, a device is disclosed that is configured to measure a soiling level characteristic of a PV array or prospective PV array.

In some embodiments, a soiling level measurement device is disclosed that does not require routine cleaning of a reference device to perform its measurement.

In some embodiments, soiling level is determined by the measurement of light from a photoemitter scattered to a photodetector by soiling particles accumulated on an exterior surface of a transparent window.

In some embodiments, a device according to the disclosed subject matter may be installed in close proximity to a PV array or at the site of prospective PV array. The soiling level detected on the device itself may be assumed to be characteristic of the soiling level on the PV array or prospective PV array. Since the accumulation of soiling particles can depend on orientation, especially tilt angle, the device may be typically installed in the same plane (same azimuth and tilt angle) as an actual or prospective PV array. In some embodiments, the device mounts onto a PV array mounting structure or onto a PV module within a PV array, especially in embodiments where a PV array is a tracking system that moves throughout the day to track the sun.

FIG. 1 depicts a device in accordance with some embodiments mounted within a photovoltaic array (100). A soiling sensor (108) and an optional irradiance sensor (106) are incorporated within a weather-resistant sealed enclosure (110). The enclosure (110) may be mounted via mounting holes (114) to a mounting bracket (112) which in turn may be mounted to a PV array mounting structure (104) in close proximity to a PV module (102) of PV array (100). Power and communication cabling (116) may pass through a cable feedthrough (150) and carry electrical power and communication signals from the device to another location from which the device is powered and to which data are reported. Enclosure (110) may be mounted such that soiling sensor (108) and optional irradiance sensor (106) are co-planar (or in a parallel plane) to PV module (102) and PV array (100).

In some embodiments, power and communication cabling (116) may comprise multiple cables entering at multiple cable feedthroughs (150). In other embodiments, the device may be self-powered, for example via an onboard solar panel, and data communication may be performed wirelessly, such that power and communication cabling (116) may be omitted.

In some embodiments, the device includes multiple soiling sensors (108) and/or multiple irradiance sensors (106).

Figure 2A:
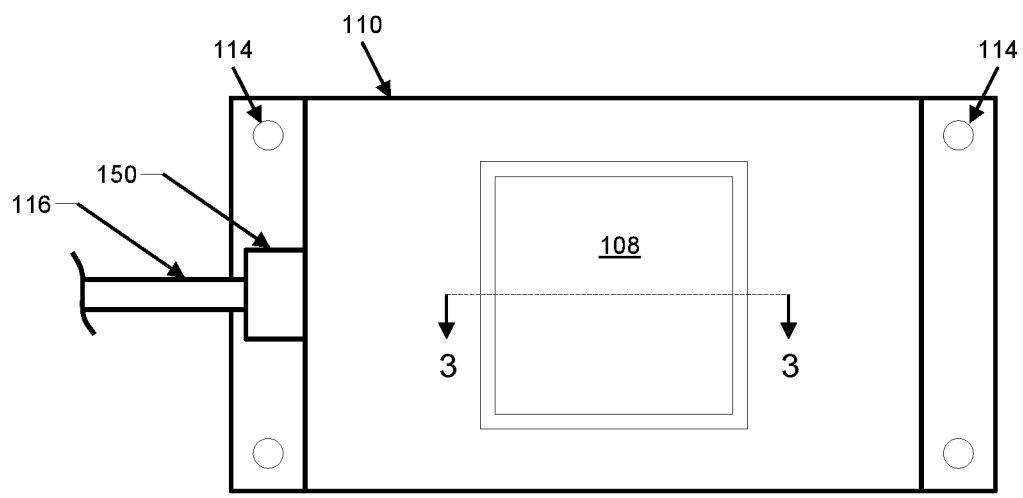
FIG. 2A depicts a top view of an embodiment comprising a soiling sensor within an enclosure.
Figure 2B:
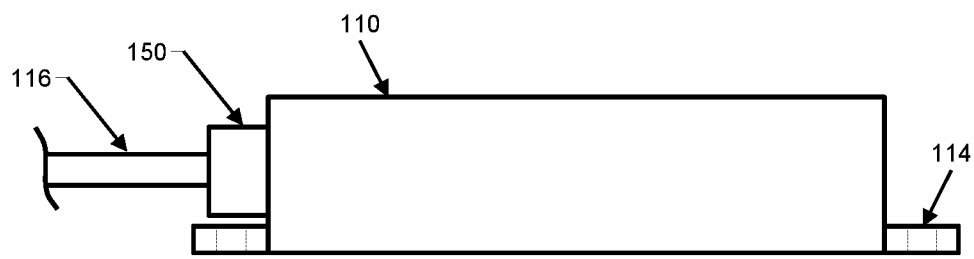
FIG. 2B depicts a side view of an embodiment depicted in FIG. 2A.

FIG. 2A and FIG. 2B depict, respectively, top and side views in accordance with some embodiments including soiling sensor (108) within enclosure (110). Enclosure (110) may be designed to be mounted, for example via mounting holes (114), outdoors at the site or prospective site of a PV array (100). One or more cable feedthroughs (150) may admit power and communications cabling (116).

Figure 3:
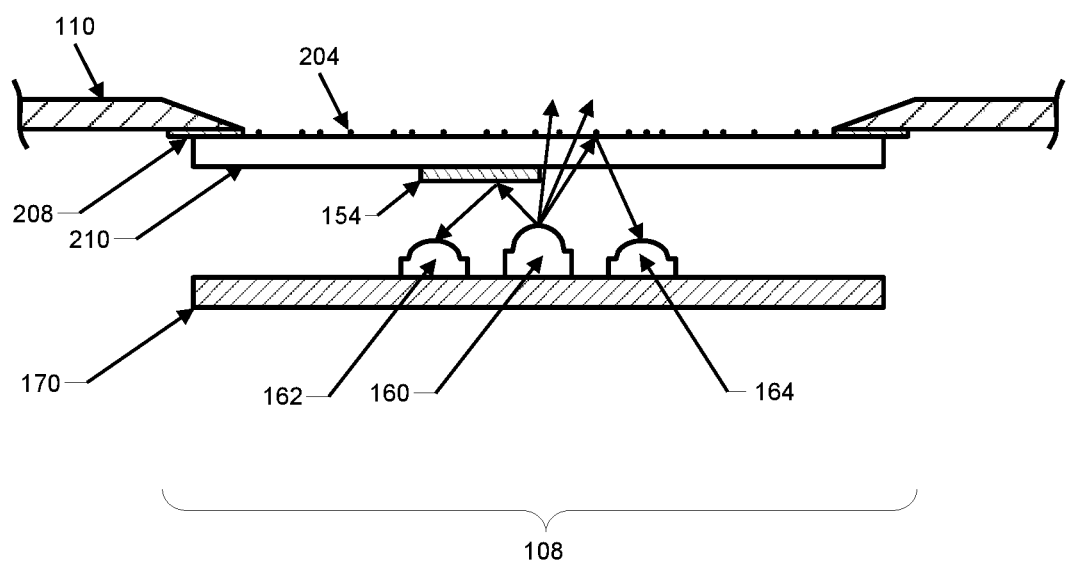
FIG. 3 depicts a cross-sectional view of an embodiment of a soiling sensor, wherein soiling particles are detected by light scattered from a photoemitter to a photodetector.

FIG. 3 depicts a cross-sectional view in accordance with some embodiments of soiling sensor (108). A transparent window (210) may be bonded to the inside of a cutout in enclosure (110) with a seal material (208), forming a window upon which soiling particles (204) may collect, in the same manner as soiling particles (204) may collect on PV array (100). Beneath transparent window (210), a photoemitter (160), photodetector (164), and optional reference photodetector (162) may be mounted on a printed circuit board (170) or other mounting means. An optional mirror (154) or reflective surface may be positioned between photoemitter (160) and optional reference photodetector (162). Photoemitter (160) emits a beam which is incident upon transparent window (210) at an angle less than the angle of total reflection and is therefore transmitted through transparent window (210). When soiling particles (204) are present on the surface of transparent window (210), light rays emitted by photoemitter (160) may be at least partially scattered to photodetector (164), yielding a measurable signal which increases with the coverage of soiling particles (204). If optional mirror (154) and optional reference photodetector (162) are included, at least a portion of the light rays emitted by photoemitter (160) may be directed via mirror (154) to reference photodetector (162); by comparing the signal detected at photodetector (164) with the signal detected at reference photodetector (162), the concentration of soiling particles (204) may be determined.

The optional use of reference photodetector (162) allows for compensation of the signal received at photodetector (164) for variations in intensity of light emitted by photoemitter (160), which may occur due to age or temperature of photoemitter (160).

Figure 4:
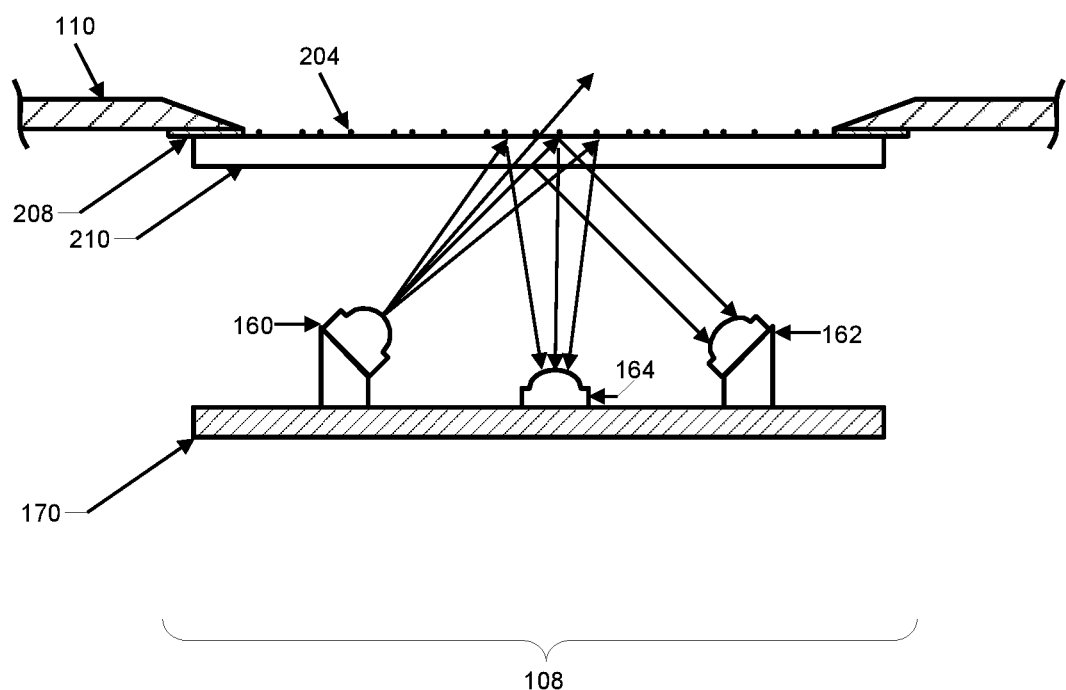
FIG. 4 depicts an alternate embodiment of a soiling sensor.

FIG. 4 depicts alternatives in accordance with some embodiments of soiling sensor (108). Photoemitter (160) may be directed at an oblique angle, less than the angle of total reflection, to the underside of transparent window (210) such that light emitted by photoemitter (160) is transmitted through transparent window (210). In the presence of soiling particles (204) a portion of the beam of light emitted by photoemitter (160) may scatter from soiling particles (204) to photodetector (164) and the signal produced by photodetector (164) may increase with the concentration of soiling particles (204). In some embodiments, reference photodetector (162) may be also included, detecting a portion of the beam of light emitted by photoemitter (160) that specularly reflects from either the top or bottom surface of transparent window (210); the signal produced by reference photodetector (162) may be used to compensate for variations in the output intensity of photoemitter (160) and the concentration of soiling particles (204) may be determined from comparison of the signal at photodetector (164) and reference photodetector (162).

Figure 5:
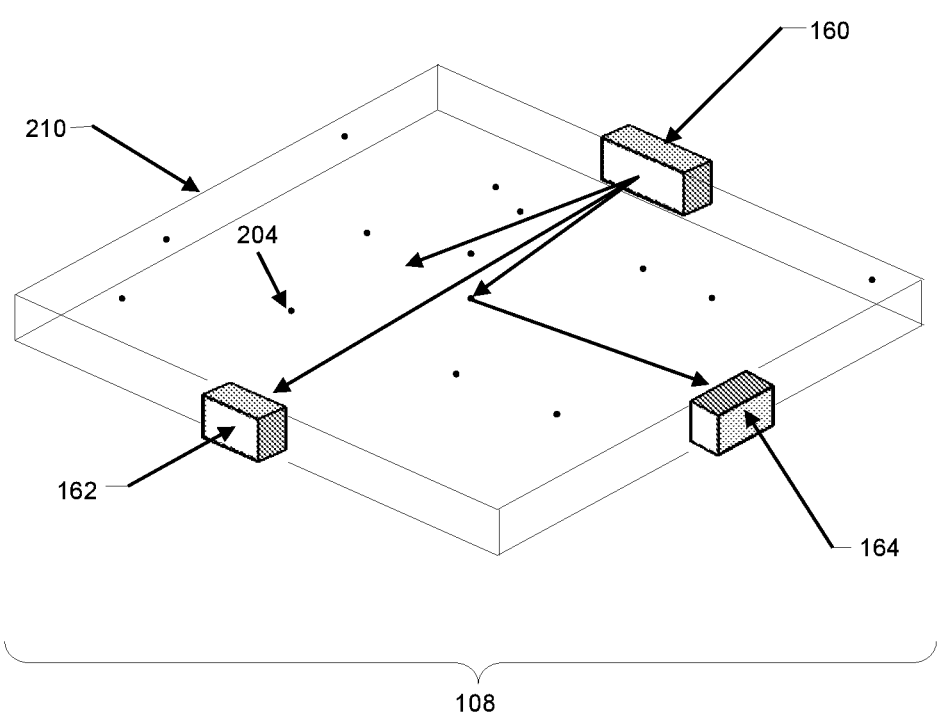
FIG. 5 depicts another alternate embodiment of a soiling sensor.

FIG. 5 depicts additional alternatives in accordance with some embodiments of soiling sensor (108), wherein photoemitter (160), photodetector (164), and optional reference photodetector (162) may be incident upon the edge faces of transparent window (210). Enclosure (110) is omitted from the figure for clarity. In the presence of soiling particles (204) on the surface of transparent window (210) some of the light rays emitted by photoemitter (160) may scatter from soiling particles (204) into photodetector (164), and the signal at photodetector (164) may increase with the concentration of soiling particles (204). In some embodiments reference photodetector (162) may be also included, detecting a portion of the light from photoemitter (160) that is not scattered. Again, by comparing the signal detected at photodetector (164) with the signal detected at reference photodetector (162), the concentration of soiling particles (204) may be determined.

In other embodiments, soiling sensor (108) may function by a combination of embodiments depicted in FIG. 3, FIG. 4, and FIG. 5, in addition to other embodiments. Combinations of the disclosed elements are intended to be within the scope of this disclosure.

Sunlight and other external lighting reaching photodetector (164) (and/or optional reference photodetector (162)) may produce a signal that interferes with the signal generated by light emitted by photoemitter (160).

In some embodiments, the effect of sunlight reaching photodetector (164) (and/or optional reference photodetector (162)) may be discriminated against by performing the measurements at night.

In some embodiments, sunlight and other external lighting may be discriminated against by operating photoemitter (160) at a wavelength that is not present or is not dominant in sunlight or in typical outdoor illumination lamps and selecting or filtering photodetector (164) and/or reference photodetector (162) to be substantially insensitive or less sensitive to other wavelengths present within sunlight. In some embodiments, filtering may be accomplished by coating transparent window (210) with filter coatings or constructing transparent window (210) of a colored glass material that provides a filter function. In some embodiments, filtering may be accomplished by incorporating a filter within the housings of photodetector (164) and/or reference photodetector (162). In an exemplary embodiment, photoemitter (160) may be an LED operating at 830 nm or 950 nm, and photodetector (164) and/or reference photodetector (162) may be photodiodes incorporating daylight-blocking filters.

In some embodiments, sunlight and other external lighting may be discriminated against by operating photoemitter (160) in a pulsed or modulated mode and signals at photodetector (164) and/or reference photodetector (162) may be detected synchronously, such that the additional signal components at photodetector (164) and/or reference photodetector (162) during the time that the photoemitter (160) is pulsed on may be recognized as the signal components due to photoemitter (160), while other signal components may be ignored or subtracted from the total. In some embodiments, photoemitter (160) may be pulsed or modulated repetitively and the signal at photodetector (164) and/or reference photodetector (162) may be measured synchronously with a lock-in detection method tuned to the pulse or modulation frequency of photoemitter (160).

In some embodiments, all or a combination of some of the above solutions may be used to discriminate against sunlight and other external lighting.

In some embodiments photoemitter (160) may be chosen to emit at infrared wavelengths (>800 nm) to maximize sensitivity to soiling particles (204) which may have higher reflectance in the infrared than in the visible region.

In some embodiments, measurements from soiling sensor (108) may be adjusted with calibration factors specific to particular types of soiling particles (204) with different spectral reflectivity which may be present at the installation site.

In some embodiments, soiling sensor (108) may be heated to remove condensation of water droplets on transparent window (210) which could interfere with the soiling sensor (108) signal.

FIG. 6A and FIG. 6B depict, respectively, top and side views in accordance with some embodiments in which an irradiance sensor (106) may be housed in enclosure (110) together with soiling sensor (108).

Figure 7:
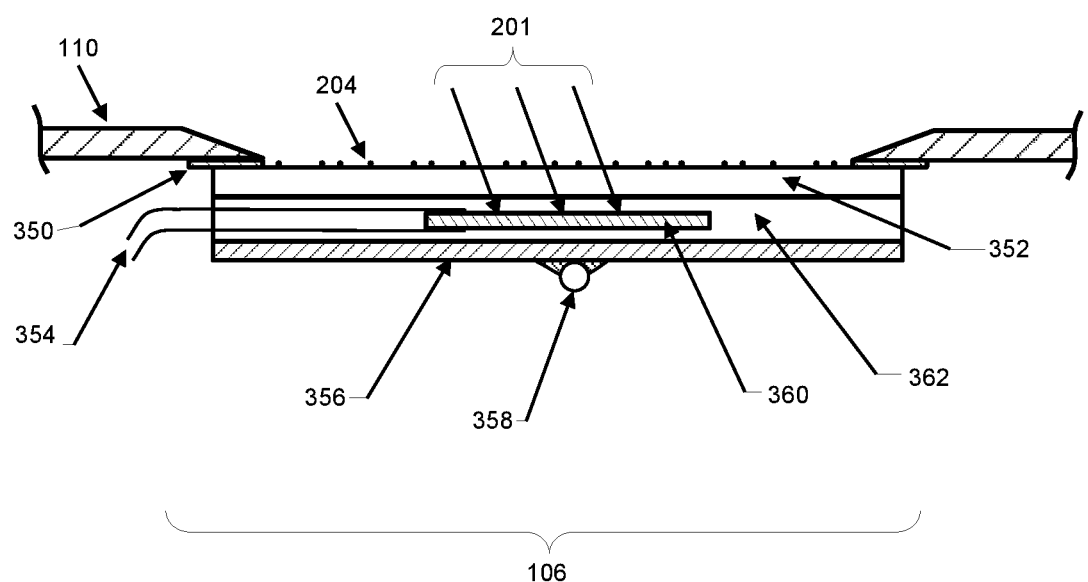
FIG. 7 depicts a cross-sectional view of an embodiment of an irradiance sensor comprising an encapsulated PV cell.

FIG. 7 depicts an irradiance sensor (106) in accordance with some embodiments. A PV cell (360) with electrical leads (354) may be encapsulated between a transparent window (352), typically fabricated of glass, and a backsheet layer (356), using a transparent encapsulant material (362). This encapsulated PV cell (360) assembly may be bonded with a seal material (350) to enclosure (110) at a window opening cut in enclosure (110), allowing sunlight (201) to illuminate PV cell (360). A temperature sensor (358), such as a Resistive Temperature Device (RTD) may measure PV cell (360) temperature. Measurement of PV cell (360) short-circuit current corrected for temperature variation may be used to determine the irradiance incident on irradiance sensor (106). In some embodiments encapsulated PV cell (360) assembly may be bonded to the inside of enclosure (110), as depicted in FIG. 7, while in other embodiments it may be bonded to the outside of enclosure (110), in order to avoid traps for the collection of soiling particles (204) following rain or washing.

Alternative embodiments of irradiance sensor (106) include, for example, a photodiode or a thermopile pyranometer.

In some embodiments, readings from soiling sensor (108) may be used to correct the readings of irradiance sensor (106) for the effects of soiling particles (204) accumulated on the surface of irradiance sensor (106), thereby improving the accuracy of irradiance sensor (106) and eliminating or reducing the need to routinely clean it.

In some embodiments, irradiance sensor (106) paired with soiling sensor (108) may be used to calibrate soiling sensor (108), by comparing readings from both irradiance sensor (106) and soiling sensor (108) before and after cleaning.

Figure 8:
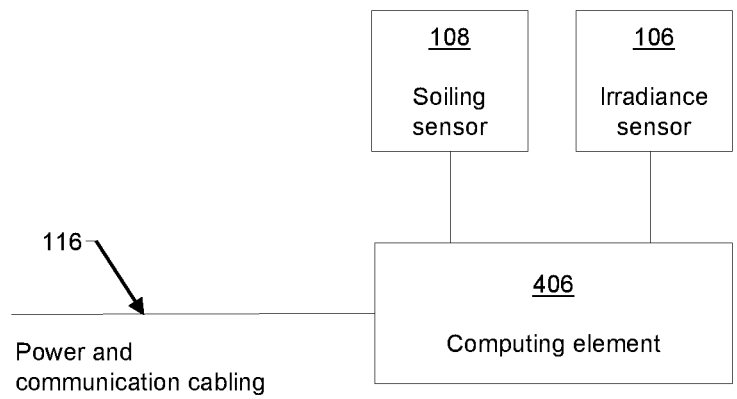
FIG. 8 depicts a block diagram of an embodiment depicted in FIG. 6A and FIG. 6B, wherein a computing element receives signals from a soiling sensor and an irradiance sensor, calculates results, and communicates a signal.

FIG. 8 depicts a block diagram of some embodiments depicted in FIG. 6A and FIG. 6B, wherein a computing element (406) may function as a measurement unit, receiving signals from soiling sensor (108) and/or irradiance sensor (106), calculating results, and communicating measurement results via power and communication cabling (116). By omitting irradiance sensor (106), the block diagram of FIG. 8 represents some embodiments of FIG. 2A and FIG. 2B.

In alternative embodiments, computing element (406) may be omitted and some of its functions may be performed by an analog and/or digital electronic circuit which may function as a measurement unit.

Although this disclosure is directed to the application of measuring soiling levels of photovoltaic arrays, it will be understood by those skilled in the art that the disclosed subject matter has other applications, including soiling and fouling of transparent windows in a variety of applications, and these additional applications are intended to be within the scope of this disclosure.

The invention claimed is:

1. A device comprising
   a soiling sensor, an irradiance sensor, and at least one measurement unit;
   wherein said irradiance sensor is configured to measure sunlight; and
   wherein said device is configured to allow soiling particles to accumulate similarly on said soiling sensor and on said irradiance sensor; and
   wherein said soiling sensor
      comprises a transparent window, a photoemitter, and a photodetector, and
      wherein said photoemitter is configured to emit light that illuminates soiling particles accumulating on a surface of said transparent window, and
      said photodetector is configured to generate a signal based at least upon detection of a portion of said light that passes through said transparent window and reflects and/or scatters from said soiling particles; and
   said at least one measurement unit determines a soiling level of said transparent window, wherein said soiling level corresponds to a fractional reduction in transmission of sunlight by said soiling particles, based at least upon a measurement of said signal of said soiling sensor; and
   wherein said at least one measurement unit is configured to calibrate said soiling sensor based at least upon comparing readings from said irradiance sensor and said soiling sensor before and after cleaning.

2. The device of claim 1, wherein said light emitted by said photoemitter is incident upon said transparent window at an angle less than the angle of total reflection.

3. The device of claim 1, wherein said photoemitter is configured to emit said light at a wavelength that is not dominant within sunlight and wherein said photodetector is configured to substantially reject light at wavelengths other than said wavelength.

4. The device of claim 1, wherein said photoemitter is configured to operate in a pulsed or modulated mode, and said signal from said photodetector is detected synchronously with said pulse or said modulation.

5. The device of claim 1, further comprising a reference photodetector which is configured to receive a portion of said light from said photoemitter and to produce a signal therefrom, and wherein said soiling level is determined by comparison of said signals from said photodetector and said reference photodetector.

6. The device of claim 1, wherein said device is configured to correct readings of said irradiance sensor by said determinations of said soiling level to account for soiling particles obscuring said irradiance sensor.

7. The device of claim 1, wherein said photoemitter and/or said photodetector are configured to be incident upon an edge face of said transparent window.

8. A method comprising
  allowing soiling particles to accumulate similarly on a surface of a transparent window and on an irradiance sensor configured to measure transmitted sunlight,
  illuminating said surface of said transparent window by emission of light from a photoemitter,
  measuring by a photodetector a portion of said light that scatters or reflects from said soiling particles on said transparent window,
  determining a soiling level of said transparent window, wherein said soiling level corresponds to a fractional reduction in light transmission, from a signal from said photodetector, and
  calibrating said soiling level at least by comparing said signal with measurements of said irradiance sensor before and after cleaning of said transparent window and/or said irradiance sensor.

9. The method of claim 8, wherein said light is incident upon said transparent window at an angle less than the angle of total reflection.

10. The method of claim 8, further comprising directing a portion of said light from said photoemitter to a reference photodetector, and determining said soiling level by comparing signals from said photodetector and said reference photodetector.

11. The method of claim 8, further comprising operating said photoemitter in a pulsed or modulated mode and detecting signals from said photodetector synchronously with said pulse or said modulation.

* * * * *